United States Patent
Zhou et al.

(10) Patent No.: US 9,702,821 B2
(45) Date of Patent: Jul. 11, 2017

(54) SURFACE ENHANCED FLUORESCENCE SPECTROSCOPY APPARATUS

(71) Applicant: Hewlett-Packard Development Company, L.P., Houston, TX (US)

(72) Inventors: Zhang-Lin Zhou, Palo Alto, CA (US); Lihua Zhao, Palo Alto, CA (US); Steven J. Barcelo, Palo Alto, CA (US); Zhiyong Li, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 14/762,415

(22) PCT Filed: Jan. 30, 2013

(86) PCT No.: PCT/US2013/023863
§ 371 (c)(1),
(2) Date: Jul. 21, 2015

(87) PCT Pub. No.: WO2014/120156
PCT Pub. Date: Aug. 7, 2014

(65) Prior Publication Data
US 2015/0355093 A1 Dec. 10, 2015

(51) Int. Cl.
*B82Y 15/00* (2011.01)
*G01N 21/64* (2006.01)
(Continued)

(52) U.S. Cl.
CPC ........... *G01N 21/648* (2013.01); *B82Y 15/00* (2013.01); *B82Y 20/00* (2013.01); *B82Y 40/00* (2013.01);
(Continued)

(58) Field of Classification Search
None
See application file for complete search history.

(56) References Cited

U.S. PATENT DOCUMENTS

| 7,344,832 B2 | 3/2008 | Henderson et al. |
| 8,105,819 B2 | 1/2012 | Moore |

(Continued)

FOREIGN PATENT DOCUMENTS

| CN | 101171504 | 4/2008 |
| CN | 101443461 | 5/2009 |

(Continued)

OTHER PUBLICATIONS

Sun et al., Composite Organic-Inorganic Nanoparticles as Raman Labels for Tissue Analysis, 2007, Nano Letters, vol. 7, No. 2, pp. 351-356.*

(Continued)

*Primary Examiner* — Erik B Crawford
(74) *Attorney, Agent, or Firm* — Mannava & Kang, P.C.

(57) ABSTRACT

According to an example, methods for forming three-dimensional (3-D) nano-particle assemblies may include depositing surface-enhanced spectroscopy (SES) elements onto respective tips of nano-fingers, in which the nano-fingers are arranged in sufficiently close proximities to each other to enable the tips of groups of adjacent ones of the nano-fingers to come into sufficiently close proximities to each other to enable the SES elements on the tips to be bonded together when the nano-fingers are partially collapsed. The methods also include causing the nano-fingers to partially collapse toward adjacent ones of the nano-fingers to cause a plurality of SES elements on respective groups of the nano-fingers to be in relatively close proximities to each other and form respective clusters of SES elements, introducing additional particles that are to attach onto the clusters of SES elements, and causing the clusters of SES elements to detach from the nano-fingers.

14 Claims, 6 Drawing Sheets

(51) Int. Cl.
*B82Y 20/00* (2011.01)
*B82Y 40/00* (2011.01)
*G01N 21/65* (2006.01)

(52) U.S. Cl.
CPC ....... *G01N 21/6428* (2013.01); *G01N 21/658* (2013.01); *G01N 2021/6441* (2013.01)

(56) References Cited

U.S. PATENT DOCUMENTS

| | | |
|---|---|---|
| 8,258,450 B1 | 9/2012 | Fries |
| 2005/0191665 A1* | 9/2005 | Su .................... G01N 33/54346 435/6.11 |
| 2008/0246961 A1 | 10/2008 | Zhang et al. |
| 2008/0316480 A1* | 12/2008 | Zhong .................... B82Y 15/00 356/301 |
| 2009/0004670 A1 | 1/2009 | Zhang et al. |
| 2009/0084162 A1 | 4/2009 | Besnard et al. |
| 2009/0142274 A1 | 6/2009 | Clark et al. |
| 2010/0112545 A1 | 5/2010 | Muralidharan et al. |
| 2010/0144557 A1 | 6/2010 | Moore |
| 2011/0166045 A1 | 7/2011 | Dhawan et al. |
| 2012/0092660 A1 | 4/2012 | Wu et al. |
| 2012/0107948 A1 | 5/2012 | Li et al. |
| 2012/0135874 A1 | 5/2012 | Wang et al. |
| 2012/0164745 A1 | 6/2012 | Fu et al. |
| 2013/0021605 A1 | 1/2013 | Yi et al. |
| 2013/0316467 A1* | 11/2013 | Carron ............. G01N 33/54313 436/501 |

FOREIGN PATENT DOCUMENTS

| | | | |
|---|---|---|---|
| CN | 101446547 | 6/2009 | |
| CN | 101529229 | 9/2009 | |
| CN | 102834709 | 12/2012 | |
| JP | 2009544967 | 12/2009 | |
| WO | WO2008013683 | 1/2008 | |
| WO | WO 2011133143 A1 * | 10/2011 | .......... G01N 21/658 |
| WO | WO-2011133143 A1 | 10/2011 | |
| WO | WO-2012054027 | 4/2012 | |
| WO | WO-2012124310 | 9/2012 | |
| WO | WO-2012128773 A1 | 9/2012 | |
| WO | WO-2012161683 A1 | 11/2012 | |

OTHER PUBLICATIONS

International Search Report and Written Opinion dated Sep. 25, 2013, issued on PCT Patent Application No. PCT/US2013/023863 file on Jan. 30, 2013, Korean Intellectual Property Office.

Yamaguchi T., et al., "Caracterization of cap-shaped silver particles for surface-enhanced fluorescence effects", Analytical Biochemistry, Feb. 24, 2007, vol. 364, p. 171-179.

European Search Report for 13873373.8-1554/2951561 dated Nov. 8, 2016.

* cited by examiner

SURFACE ENHANCED FLUORESCENCE SPECTROSCOPY APPARATUS

CLAIM FOR PRIORITY

The present application is a national stage filing under 35 U.S.C 371 of PCT application number PCT/US2013/023863, having an international filing date of Jan. 30, 2013, the disclosure of which is hereby incorporated by reference in its entirety.

BACKGROUND

Spectroscopy, which broadly refers to the interaction between energy and matter, may be used for such purposes as chemical and biological sensing. In a typical spectroscopy measurement, incident radiation (photons, for example) is directed to a particular analyte (i.e., a species, molecule, compound, biological or non-biological specimens, or, in general, matter being analyzed). The molecules in the analyte can inelastically scatter (Raman scatter) the incident radiation or the molecules can emit photons (luminescence, fluorescence, etc.) as a result of absorbing the incident photons.

BRIEF DESCRIPTION OF THE DRAWINGS

Features of the present disclosure are illustrated by way of example and not limited in the following figure(s), in which like numerals indicate like elements, in which.

DETAILED DESCRIPTION

Figure 1A:
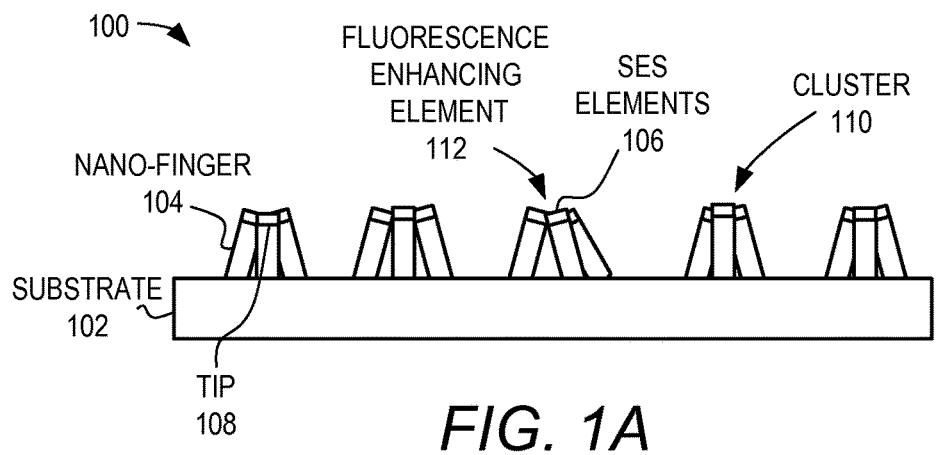
FIG. 1A shows a simplified side view of a surface-enhanced fluorescence spectroscopy (SEFS) apparatus, according to an example of the present disclosure.

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure.

Throughout the present disclosure, the terms "a" and "an" are intended to denote at least one of a particular element. As used herein, the term "includes" means includes but not limited to, the term "including" means including but not limited to. The term "based on" means based at least in part on. In addition, the term "light" refers to electromagnetic radiation with wavelengths in the visible and non-visible portions of the electromagnetic spectrum, including infrared, near infrared, and ultra-violet portions of the electromagnetic spectrum.

Disclosed herein are methods for forming a surface-enhanced fluorescence spectroscopy (SEFS) apparatus and SEFS apparatuses formed through implementation of the methods. In the methods and SEFS apparatuses, a plurality of surface-enhanced spectroscopy (SES) elements may be deposited onto respective tips of a plurality of nano-fingers, in which the nano-fingers are arranged in sufficiently close proximities to each other to enable the tips of a group of adjacent nano-fingers to come into sufficiently close proximities to each other to enable the SES elements on the tips to trap fluorescence enhancing elements when the nano-fingers are partially collapsed. In addition, the fluorescence enhancing elements may be introduced between the plurality of SES elements and the nano-fingers in the group of adjacent nano-fingers may be caused to partially collapse toward each other to cause a plurality of SES elements on the tips of the nano-fingers in the group to come into sufficiently close proximities to each other to trap a fluorescence enhancing element of the fluorescence enhancing elements between the plurality of SES elements.

Through the partial collapse of the nano-fingers onto other ones of the nano-fingers, for instance, in a controlled manner, the SES elements positioned on various groups of the nano-fingers may be brought into sufficiently close proximities to enable those SES elements to trap fluorescence enhancing elements therebetween. In one regard, the use of the nano-fingers in trapping the fluorescence enhancing elements may generally enable groups of SES elements to be arranged in tightly packed configurations and may increase the likelihood that the fluorescence enhancing elements are located sufficiently close the SES elements to enhance fluorescence emissions by target molecules.

The enhanced fluorescence spectroscopy available through implementation of the SEFS apparatus disclosed herein may be implemented in the detection of chemical and/or biological analytes. In one regard, the SEFS apparatus disclosed herein may be implemented in chemical and/or biological sensors in which the target analytes do not scatter Raman signals (such as metal ions) or generate substantially complex Raman peaks (such as relatively large molecular weight biological species). In addition, because different types of fluorescence enhancing elements may be trapped between the SES elements, the fluorescence enhancing elements may be selected to be highly selective and sensitive to particular types and/or species of analytes. In other words, the fluorescence enhancing elements to be used in the SEFS apparatus may be selected based on the particular type and/or species of the analytes to be detected.

According to an example, metal oxide layers may be provided on the SES elements to protect the SES elements during enhanced fluorescence spectroscopy operations. The metal oxide layers may be formed on the SES elements prior to the partial collapsing of the nano-fingers.

Generally speaking, fluorescence may be defined as the emission of light by a substance that has absorbed light or other electromagnetic radiation and may be considered as a form of luminescence. In most cases, the emitted light has a longer wavelength, and therefore lower energy, than the absorbed radiation. In other cases, such as when the absorbed electromagnetic radiation is relatively intense, one electron may absorb two photons. This two-photon absorption may lead to emission of radiation having a shorter wavelength than the absorbed radiation. In still other cases, the emitted radiation may be of the same wavelength as the absorbed radiation, which may be termed "resonance fluorescence".

With reference first to FIG. 1A, there is shown a simplified side view of a surface-enhanced fluorescence spectroscopy (SEFS) apparatus 100, according to an example. It should be understood that the SEFS apparatus 100 depicted in FIG. 1A may include additional components and that some of the components described herein may be removed and/or modified without departing from a scope of the SEFS apparatus 100 disclosed herein. It should also be understood that the components depicted in FIG. 1A may not be drawn to scale and thus, the components may have different relative sizes with respect to each other than as shown therein.

The SEFS apparatus 100 may include a substrate 102 and a plurality of nano-fingers 104 that extend above a surface of the substrate 102. In FIG. 1A, the nano-fingers 104 may be depicted following a partial collapsing of the nano-fingers 104 onto each other as discussed in greater detail below.

The SEFS apparatus 100 may also include a plurality of surface-enhanced spectroscopy (SES) elements 106 positioned on tips 108 of the nano-fingers 104. As discussed below, the SES elements 106 may be positioned on the tips 108 of the nano-fingers 104 prior to the nano-fingers 104 being partially collapsed. As such, as the nano-fingers 104 partially collapse toward each other, the SES elements 106 positioned on the tips 108 may also be in relatively close proximities (e.g., sub-nanometer distances apart) and/or in contact with each other. The SES elements 106 that are in relatively close proximities and/or in contact with each other may be considered as being in respective clusters 110 of SES elements 106. According to an example, the SES elements 106 in a cluster 110 may be in sufficiently close proximity to the other SES elements 106 in the cluster 110 to enable the SES elements 106 in the cluster 110 to be bonded to each other through either or both of gold-gold bonding and binding molecules (not shown), such as dithiol, diamine, etc.

Generally speaking, the SES elements 106 may be elements that enhance the emission of light (e.g., Raman scattering, fluorescence, luminescence, etc.), by particles in contact with and/or in relatively close proximities to the SES elements 106 and therefore enhance sensing operations, such as surface enhanced Raman spectroscopy (SERS), enhanced photoluminescence, enhanced fluorescence, etc., on the particles. The SES elements 106 may include, for instance, plasmonic nanoparticles or nanostructures, which may be plasmon-supporting materials such as but not limited to, gold (Au), silver (Ag), and copper (Cu).

The SES elements 106 may have nanoscale surface roughness, which may generally be characterized by nanoscale surface features on the surface of the layer(s) and may be produced spontaneously during deposition of the plasmon-supporting material layer(s). By definition herein, a plasmon-supporting material may be a material that facilitates scattering of signals and the production or emission of a signal from an analyte on or near the material during spectroscopy.

In some examples, the SES elements 106 may be functionalized to facilitate adsorption of target molecules. For example, surfaces of the SES elements 106 may be functionalized such that a particular class of analytes may be attracted to and may bond or be preferentially adsorbed onto the SES elements 106. By way of particular example, the SES elements 106 may be functionalized to attach to target molecules that may be contained in, for instance, particular types of cells, tissues, etc.

Figure 1B:
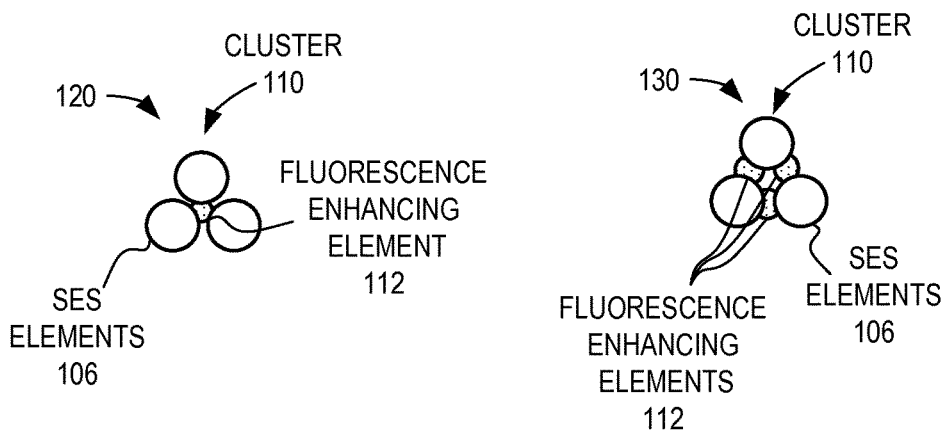
FIGS. 1B and 1C, respectively show simplified diagrams, for instance, viewed from a top of a portion of the SEFS apparatus in FIG. 1A, of various example configurations of the clusters of surface-enhanced spectroscopy (SES) elements, in which a fluorescence enhancing element may be trapped between the SES elements, according to examples of the present disclosure.
Figure 1C:
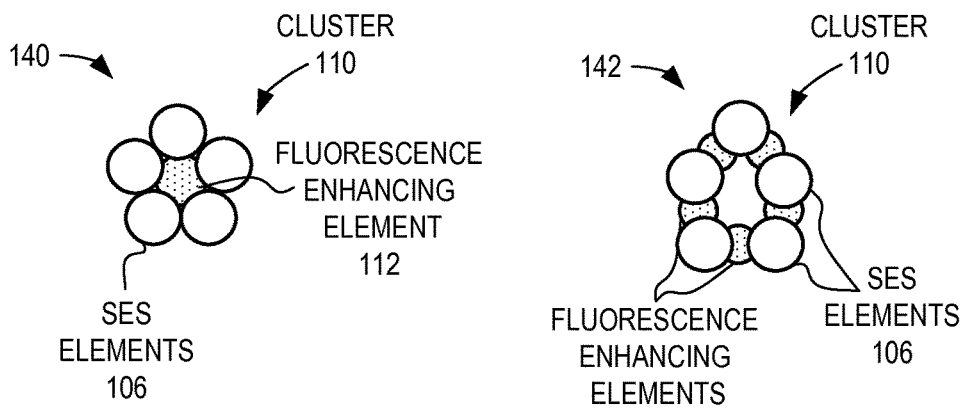

Turning now to FIGS. 1B and 1C, there are shown simplified diagrams, for instance, viewed from a top of a portion of the SEFS apparatus 100 in FIG. 1A, of various example configurations of the clusters 110 of SES elements 106, in which a fluorescence enhancing element 112 may be trapped between the SES elements 106, according to various examples. Generally speaking, the diagrams depicted in FIGS. 1B and 1C illustrate examples of possible arrangements of the SES elements 106 (and the fluorescent element 112) that may result when the nano-fingers 104 are partially collapsed as shown in FIG. 1A following introduction of the fluorescence enhancing elements 112. It should thus be understood that the diagrams depicted in FIGS. 1B and 1C are provided merely for purposes of illustration and that any number of alternate configurations, which may include other numbers of SES elements 106 and/or fluorescence enhancing elements 112 than as shown therein, may be formed without departing from scopes of examples of the present disclosure.

Generally speaking, the fluorescence enhancing element 112 may be an element that may enhance detection of chemical and/or biological target molecules. For instance, the fluorescence enhancing element 112 may be an element that enhances the fluorescence of target molecules that are in relatively close proximity to the cluster 110 of SES elements 106 in which the fluorescent element 112 is trapped. In other examples, the fluorescence enhancing element 112 may be an element that itself does not enhance fluorescence, but enhances fluorescence when binded with another particle or molecule. Examples of fluorescence enhancing elements 112 that may enhance fluorescence individually and/or through binding with other particles or molecules are discussed herein.

The fluorescence enhancing element 112 may be any of a fluorescent dye, a fluorescent probe, a fluorescent probe that has been binded to a target molecule, a non-fluorescent ion indicator, a non-fluorescent ion indicator binded to a metal ion, etc. In any regard, a fluorescent element 112 may be introduced between the SES elements 106 prior to the partial collapse of the nano-fingers 104 such that the fluorescence enhancing element 112 may be trapped between the SES elements 106 once the nano-fingers 104 are partially collapsed. In addition, in examples in which the fluorescence enhancing element 112 includes a combination of elements, one of the elements may be introduced prior to the partial collapse of the nano-fingers 104 and another one of the elements may be introduced following the partial collapse of the nano-fingers 104. In these examples, the fluorescence enhancing element 112 may not enhance fluorescence until the elements are binded together.

With reference first to FIG. 1B, a first diagram 120 illustrates an example in which a fluorescence enhancing element 112 may be trapped between three SES elements 106 of a cluster 110. A second diagram 130 illustrates an example in which three fluorescence enhancing elements 112 may be trapped between each of the three SES elements 106 of a cluster 110. As shown in FIG. 1C, a first diagram 140 illustrates an example in which a fluorescence enhancing element 112 may be trapped between five SES elements 106 of a cluster 110. In addition, a second diagram 142 illustrates an example in which five fluorescence enhancing elements 112 may be trapped between five SES elements 106 of a cluster 110. Although not shown in FIGS. 1B and 1C, fluorescence enhancing elements 112 may be trapped between some but not all of the SES elements 106 of a cluster 110. In addition, or alternatively, some of the SES elements 106 of a cluster 110 may be bonded to each other through gold-gold bonding and/or through binding molecules (not shown).

Figure 2:
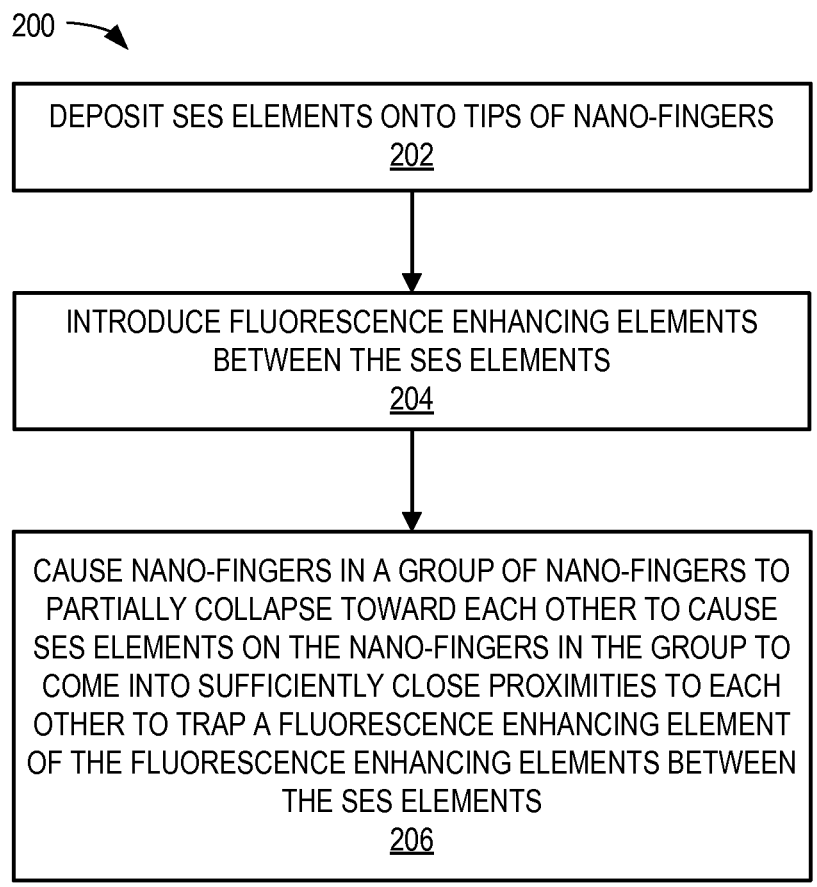
FIG. 2 shows a flow diagram of a method for forming a SEFS apparatus, according to an example of the present disclosure.

Turning now to FIG. 2, there is shown a flow diagram of a method 200 for forming a SEFS apparatus 100, according to an example. It should be understood that the method 200 depicted in FIG. 2 may include additional processes and that some of the processes described herein may be removed and/or modified without departing from a scope of the method 200. Examples of various additional processes that may be implemented with respect to the method 200 are provided below.

At block 202, a plurality of SES elements 106 may be deposited onto the tips 108 of a plurality of nano-fingers 104, in which the plurality of nano-fingers 104 extend from a substrate 102 and may be arranged in sufficiently close proximities to each other to enable the tips 108 of a group of adjacent nano-fingers 104 to come into sufficiently close proximities to each other to enable the SES elements 106 on the tips 108 to trap fluorescence enhancing elements 112 when the nano-fingers 104 are partially collapsed. That is, the plurality of nano-fingers 104 in a group of nano-fingers 104 may be in sufficiently close proximities to each other to enable the SES elements 106 on the tips 108 of those nano-fingers 104 to trap a fluorescence enhancing element 112 between the SES elements 106 when the nano-fingers 104 in the group are partially collapsed. By way of example, groups of the nano-fingers 104 may be in sufficiently close proximities to enable the SES elements 106 on the nano-fingers 104 of the respective groups to be positioned with distances that are below about one nanometer.

At block 204, fluorescence enhancing elements 112 may be introduced between the SES elements 106. According to an example, the fluorescence enhancing elements 112 may be contained in a solution, which may be provided onto the substrate 102, the nano-fingers 104, and the SES elements 106. In another example, the substrate 102, the nano-fingers 104, and the SES elements 106 may be provided, e.g., dipped, into a solution containing the fluorescence enhancing elements 112.

At block 206, the nano-fingers 104 in the group of adjacent nano-fingers 104 may be caused to partially collapse toward each other to cause a plurality of SES elements 106 on the tips 108 of the nano-fingers 104 in the group to come into sufficiently close proximities (e.g., less than about one nanometer) to each other to trap a fluorescence enhancing element 112 of the fluorescence enhancing elements 112 between the plurality of SES elements 106. As discussed herein, the nano-fingers 104 may be fabricated on the substrate 102 such that the nano-fingers 104 in respective groups may partially collapse toward each other (and thus may not partially collapse toward nano-fingers 104 in other groups). As also discussed herein, the nano-fingers 104 may be caused to partially collapse toward each other through introduction and removal of a fluid between the nano-fingers 104.

Figure 3A:
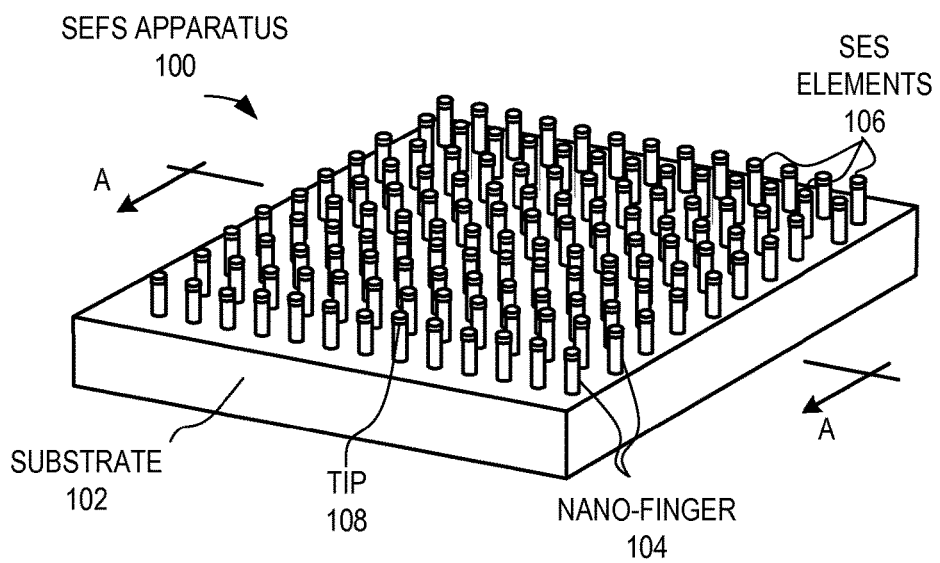
FIGS. 3A and 3B, respectively show a simplified isometric view and a simplified cross-sectional view taken along lines A-A of FIG. 3A of a SEFS apparatus, in which FIGS. 3A and 3B, along with FIG. 1A, depict various fabrication stages of the SEFS apparatus, according to examples of the present disclosure.
Figure 3B:
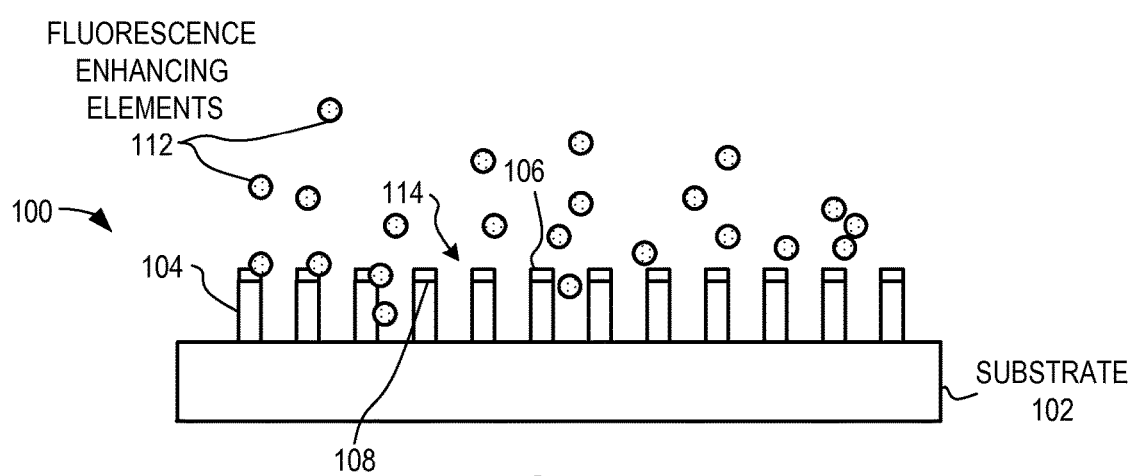

With reference now to FIGS. 3A and 3B, there are respectively shown an isometric view and a cross-sectional view taken along lines A-A of FIG. 3A of a SEFS apparatus 100, in which FIGS. 3A and 3B, along with FIG. 1A, depict various fabrication stages of the SEFS apparatus 100, according to an example. In one regard, therefore, the diagrams in FIGS. 1A, 3A, and 3B may show the operations performed in the method 200 along with some variations to those operations. It should be understood that the SEFS apparatus 100 depicted in FIGS. 3A and 3B may include additional components and that some of the components described herein may be removed and/or modified without departing from a scope of the SEFS apparatus 100 disclosed herein. It should also be understood that the components depicted in FIGS. 3A and 3B are not drawn to scale and thus, the components may have different relative sizes with respect to each than as shown therein.

The SEFS apparatus 100 depicted in FIGS. 3A and 3B may include the same features as those depicted in FIG. 1A. The SEFS apparatus 100 depicted in FIG. 3A may differ from the SEFS apparatus 100 depicted in FIG. 1A in that the nano-fingers 104 in the SEFS apparatus 100 depicted in FIG. 3A may be in a pre-collapsed state. In one regard, FIG. 3A may depict the SEFS apparatus 100 following block 202 in FIG. 2, in which the SES elements 106 may be deposited onto the tips 108 of the nano-fingers 104.

The substrate 102 may be formed of a material, such as, silicon, silicon nitride, glass, quartz, sapphire, diamond, diamond-like carbon, plastic, polymer, silicon dioxide ($SiO_2$), aluminum oxide ($Al_2O_3$), aluminum, a combination of these materials, etc. The substrate 102 may be in a form selected from the group consisting of a sheet, a wafer, a film, and a web. For example, if the substrate 102 is in the form of a web, the substrate 102 may be used as feed stock, as rolls of material in a roll-to-roll fabrication process. As another example, the substrate 102 may be in the form of a flexible polymer film composed of a plastic material, such as polyimide, polyethylene, polypropylene, or some other suitable polymeric plastic. Thus, in accordance with an example, the substrate 102 may be either rigid, as for a semiconductor wafer, or flexible, as for the web.

The nano-fingers 104 may have dimensions that are in the nanometer range, for instance, dimensions that may be less than about 500 nm, and may be formed of a relatively flexible material and/or have a relatively high aspect ratio to enable the nano-fingers 104 to be laterally bendable or collapsible, for instance, to enable tips of the nano-fingers 104 to be in relatively close proximities with respect to each other as shown in FIG. 1A. For instance, the tips of the nano-fingers 104 that are in relatively close proximities to each other may have gaps therebetween that are sub-nanometer in size when the nano-fingers 104 are partially collapsed. Examples of suitable materials for the nano-fingers 104 may include polymer materials, such as, UV-curable or thermal curable imprinting resist, polyalkylacrylate, polysiloxane, polydimethylsiloxane (PDMS) elastomer, polyimide, polyethylene, polypropelene, polyurethane, fluoropolymer, etc., or any combination thereof, metallic materials, such as, gold, silver, aluminum, etc., semiconductor materials, etc., and combinations thereof.

The nano-fingers 104 may be attached to the surface of the substrate 102 through any suitable attachment mechanism. For instance, the nano-fingers 104 may be grown directly on the substrate 102 surface through implementation of any of a variety of suitable nano-structure growing techniques. As another example, the nano-fingers 104 may be integrally formed with the substrate 102. In this example, for instance, a portion of the material from which the substrate 102 may be fabricated may be etched or otherwise processed to form the nano-fingers 104. In a further example, a separate layer of material may be adhered to the substrate 102 surface and the separate layer of material may be etched or otherwise processed to form the nano-fingers 104. In various examples, the nano-fingers 104 may be fabricated through a nanoimprinting or an embossing process in which a template of relatively rigid pillars may be employed in a multi-step imprinting process on a polymer matrix to form the nano-fingers 104. In these examples, a template may be formed through photolithography or other advanced lithography with the desired patterning to arrange the nano-fingers 104 in the predetermined arrangement. More particularly, for instance, the desired patterns may be designed on a mold by any of E-beam lithography, photolithography, laser interference lithography, Focused Ion Beam (FIB), self-assembly of spheres, etc. In addition, the pattern may be transferred onto another substrate, for instance, a silicon, glass, or polymer substrate (polydimethylsiloxane (PDMS), polyimide, polycarbonate, etc.). Various other processes, such as, etching, and various techniques used in the fabrication of micro-electromechanical systems (MEMS) and nano-electromechanical systems (NEMS) may also be used to fabricate the nano-fingers 104.

The nano-fingers 104 may be arranged in a substantially random distribution or the nano-fingers 104 may be arranged in a predetermined configuration. In any regard, according to an example, the nano-fingers 104 may be arranged with respect to each other such that the tips of at least two neighboring nano-fingers 104 are able to be brought into close proximity with each other when the nano-fingers 104 are in a partially collapsed state. By way of particular example, the neighboring nano-fingers 104 may be positioned less than about 100 nanometers apart from each other. According to a particular example, the nano-fingers 104 may be patterned on the substrate 102 such that neighboring ones of the nano-fingers 104 preferentially partially collapse into predefined geometries, for instance, triangles, squares, pentagons, etc.

Turning now to FIG. 3B, there is shown a cross-sectional view along a line A-A in FIG. 3A of the apparatus 100, in accordance with an example. As shown therein, each of the tips 108 of the nano-fingers 104 may include a respective SES element 106 disposed thereon. The SES elements 106, which may include metallic nanoparticles as discussed below, may be deposited onto the tips 108 of the nano-fingers 104 through one of, for instance, physical vapor deposition (PVD), chemical vapor deposition (CVD), sputtering, etc., of metallic material, or self-assembly of pre-synthesized nano-particles.

Although the nano-fingers 104 have been depicted in FIGS. 3A and 3B as each extending vertically and at the same heights with respect to each other, it should be understood that some of the nano-fingers 104 may extend at various angles and heights with respect to each other. The differences in angles and/or heights between the nano-fingers 104 may occur, for instance, due to differences arising from manufacturing or growth variances existent in the fabrication of the nano-fingers 104 and the deposition of the SES elements 106 on the nano-fingers 104, etc.

As shown in FIGS. 3A and 3B, the nano-fingers 104 are in a first position, in which the tips 108 are in a substantially spaced arrangement with respect to each other, e.g., with gaps 114 between the tips 108. The gaps 114 between the tips 108 may be of sufficiently large size to enable a liquid, such as a liquid or solution containing fluorescence enhancing elements 112 to be positioned in the gaps 114. In addition, the gaps 114 may be of sufficiently small size to enable the tips 108 of at least some of the nano-fingers 104 to be drawn toward each other as the liquid provided in the gaps 114 evaporates, through, for instance, capillary or microcapillary forces applied on the nano-finger 104. In one regard, FIG. 3B may depict the SEFS apparatus 100 following block 204 in FIG. 2, in which the fluorescence elements 112 may be introduced between the SES elements 106. In addition, the liquid or solution may also contain binding molecules that may cause the SES elements 106 in respective clusters 110 to bind to each other.

Following at least partial evaporation of the liquid or solution containing the fluorescence enhancing elements 112, the nano-fingers 104, SES elements 106, and the fluorescence enhancing elements 112 may have the configuration as shown in FIG. 1A. That is, the fluorescence enhancing elements 112 may be trapped between SES elements 106 of respective clusters 110 of SES elements 106. In one regard, FIG. 3C may depict the SEFS apparatus 100 following block 206 in FIG. 2, in which the nano-fingers 104 in respective groups of adjacent nano-fingers may be caused to partially collapse toward each other to cause a plurality of SES elements on the tips of the nano-fingers in the respective groups to come into sufficiently close proximities to each other to trap fluorescence enhancing elements between the plurality of SES elements.

The nano-fingers 104 have been depicted as having substantially cylindrical cross-sections. It should, however, be understood that the nano-fingers 104 may have other shaped cross-sections, such as, for instance, rectangular, square, triangular, etc. By way of example, the nano-fingers 104 may have conical configurations in which the bases are attached to the substrate 102 and the tips extend away from the substrate 102. In addition, or alternatively, the nano-fingers 104 may be formed with a feature, such as, notches, bulges, etc., to substantially cause the nano-fingers 104 to be inclined to collapse in particular directions. Thus, for instance, two or more adjacent nano-fingers 104 may include features to increase the likelihood that the nano-fingers 104 collapse toward each other.

According to a particular example, groups of two or more adjacent nano-fingers 104 may include features or may otherwise be fabricated to collapse toward each other, such that the tips on the two or more adjacent nano-fingers 104 may come into relatively close proximities to each other when the nano-fingers 104 are partially collapsed. In other examples, the nano-fingers 104 are arranged on the substrate 102 such that groups of the nano-fingers 104 are in relatively closer proximities to each other than with the nano-fingers 104 outside of the groups. In this regard, when a fluid is introduced onto the nano-fingers 104 and the fluid evaporates, the nano-fingers 104 in the respective groups may collapse toward each other due to the greater microcapillary forces applied onto those nano-fingers 104. Various manners in which the nano-fingers 104 may be partially collapsed are described in greater detail herein below.

According to an example, the fluorescence enhancing elements 112 may be a fluorescent dye. In this example, a solution containing the fluorescent dye and a solvent may be introduced between the SES elements 106 at block 204 in FIG. 2. Examples of the fluorescent dye may be, but not limited to, Rhodamine based fluorescent dyes such as Alexa Fluor 488 dye, Alexa Fluor 500 dye, Alexa Fluor 514 dye, Alexa Fluor 532 dye, Alexa Fluor 546 dye, Alexa Fluor 555 dye, Alexa Fluor 568 dye, Alexa Fluor 594 dye, Alexa Fluor 610 dye, Alexa Fluor 633 dye, Alexa Fluor 635 dye, Alexa Fluor 647 dye, Alexa Fluor 660 dye, Alexa Fluor 680 dye, Alexa Fluor 700 dye, Alexa Fluor 750 dye, Alexa Fluor 350 dye, Alexa Fluor 405 dye, Alexa Fluor 430 dye from Molecular Probes; BODIPY fluorophore based fluorescent dyes such as BODIPY 493/503, BODIPY R6G, BODIPY TMR, BODIPY 558/568, BODIPY 564/570, BODIPY 576/589, BODIPY 581/591, BODIPY TR, BODIPY 630/650, BODIPY 650/655; Fluorescein based fluorescent dyes such as Oregon Green 488 carboxylic acid, Oregon Green 514 carboxylic acid; and other coumarin or pyrene based fluorescent dyes. In this example, the solvent may be evaporated at block 206, thereby leaving the fluorescent dye trapped between some of the SES elements 106.

According to another example, the fluorescence enhancing elements 112 may be fluorescent probe molecules that are to bind with target molecules. The fluorescent probe molecules may represent any molecules that give certain color changes or emit different fluorescent color with or without an associated target molecule. The fluorescent probe molecules may have a receptor unit that may selectively bind to certain chemical or biological agents, such as crown ether for metal ions, etc. The target molecules may refer to any target molecules that are of interest, which may be soluble in common solvents. By way of example, the target molecules may include melamine, pesticides, Ractopamine, etc. Common solvents may include methanol, ethanol, isopropanol, hexafluoro-isopropanol, toluene, chloroform, tetrahydrofuran, acetone, acetonitrile, xylenes, ethyl acetate, hexanes, dichloromethane, etc. For instance, the fluorescent probe molecules may not have any fluorescence but may show relatively strong fluorescence when the fluorescent probe molecules bind to target molecules.

Figure 4A:
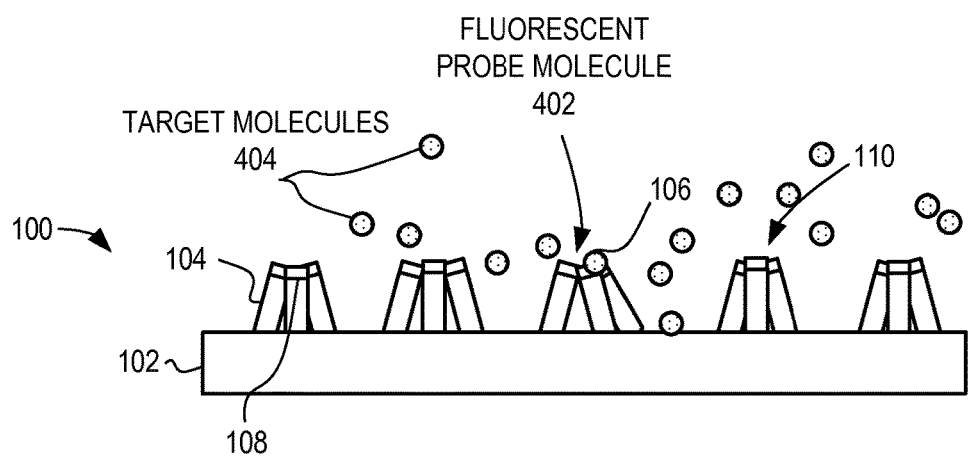
FIG. 4A shows a simplified side view of a SEFS apparatus in which fluorescent probe molecules may have been trapped between the SES elements in the respective clusters of SES elements of FIG. 1A, according to an example of the present disclosure.

In one example, the target molecules 404 may be introduced following the partial collapse of the nano-fingers 104. This example is depicted in FIG. 4A, which shows a simplified side view of a SEFS apparatus 100 in which fluorescent probe molecules 402 may have been trapped between the SES elements 106 in the respective clusters 110 of SES elements 106, according to an example. In FIG. 4A, a solution containing the target molecules 404 may be introduced to bind with the fluorescent probe molecules 402 following the trapping of the fluorescent probe molecules 402 between the SES elements 106. In this example, the target molecules 404 may bind to the fluorescent probe molecules 402, for instance, because the fluorescent probe molecules 402 may include receptor units that are selectively bind to the target molecules.

Figure 4B:
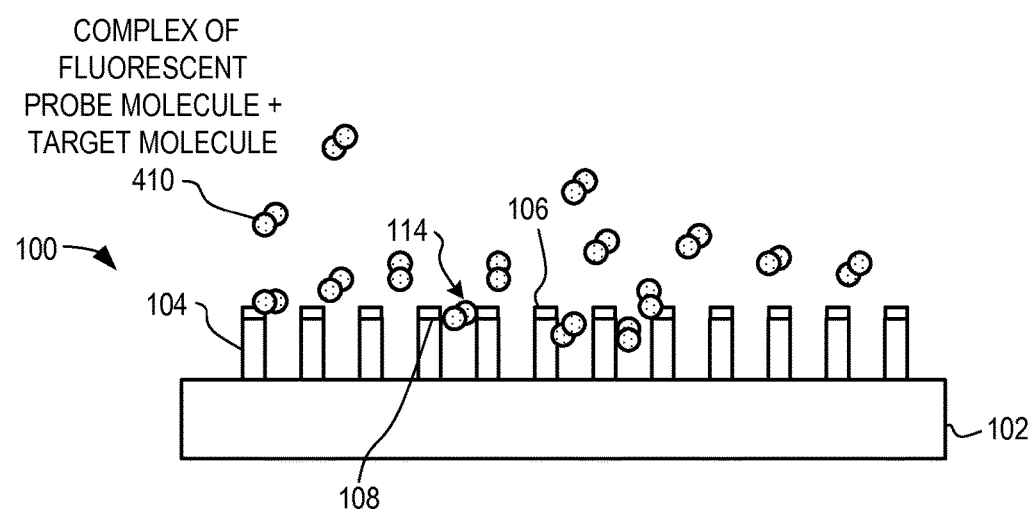
FIG. 4B shows a simplified side view of a SEFS apparatus in which a solution containing complexes of fluorescent probe molecules and target molecules may be introduced between the SES elements of respective clusters of SES elements of FIG. 1A, according to an example of the present disclosure.

In another example, the fluorescent probe molecules 402 and the target modules 404 may be combined into complexes 410 prior to the partial collapse of nano-fingers 104. This example is depicted in FIG. 4B, which shows a simplified side view of a SEFS apparatus 100 in which a solution containing complexes 410 of fluorescent probe molecules 402 and target molecules 404 may be introduced between the SES elements 106 of respective clusters 110 of SES elements 106. In this example, following the partial collapse of the nano-fingers 104, for instance, at block 206 in FIG. 2, the combinations 410 may be trapped between the SES elements 106.

Figure 5A:
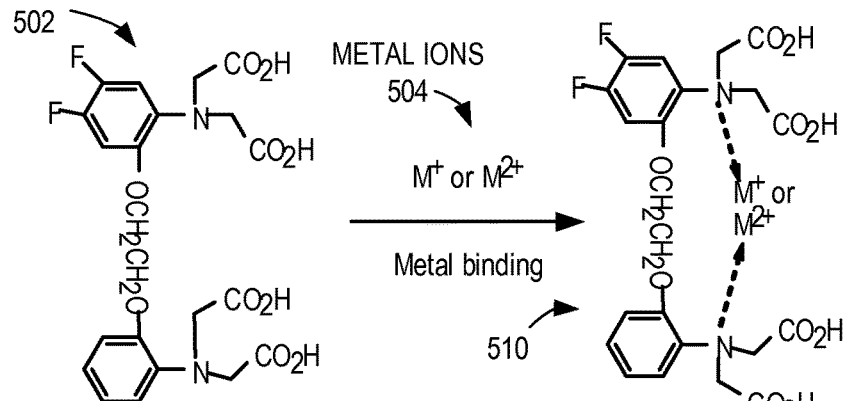
FIG. 5A shows chemical structures of a non-fluorescent ion indicator binding with metal ions to form a complex, according to an example of the present disclosure.

According to a further example, the fluorescence enhancing elements 112 may be complexes 510 formed of non-fluorescent ion indicators 502 that are selectively binded to predetermined metal ions 504. In this example, the complexes 510 may exhibit relatively strong fluorescence. An example of the chemical structures of a non-fluorescent ion indicator 502 binding with metal ions 504 to form a complex 510 is depicted in FIG. 5A.

Figure 5B:
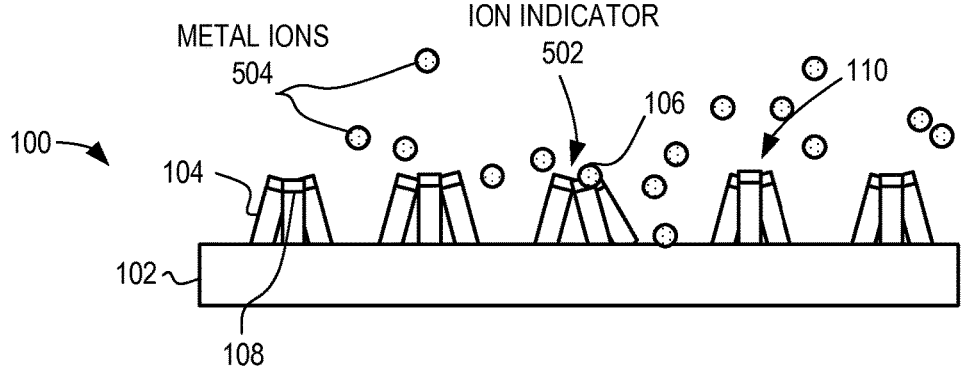
FIG. 5B shows a simplified side view of a SEFS apparatus 100 in which non-fluorescent ion indicators may have been trapped between the SES elements in respective clusters of SES elements in FIG. 1A, according to an example of the present disclosure.

In one example, the metal ions 504 may be introduced following the partial collapse of the nano-fingers 104. This example is depicted in FIG. 5B, which shows a simplified side view of a SEFS apparatus 100 in which non-fluorescent ion indicators 502 may have been trapped between the SES elements 106 in respective clusters 110 of SES elements 106, according to an example. In FIG. 5B, a solution containing the metal ions 504 may be introduced to bind with the non-fluorescent ion indicators 502 following the trapping of the non-fluorescent ion indicators 502 between the SES elements 106.

Figure 5C:
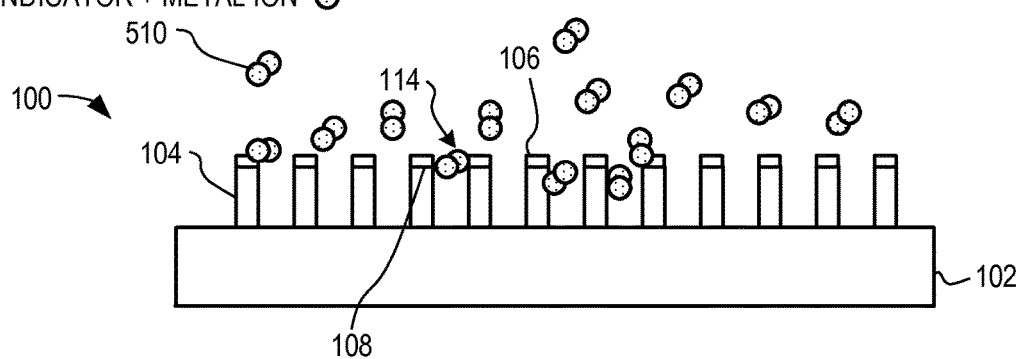
FIG. 5C shows a simplified side view of a SEFS apparatus in which a solution containing complexes of non-fluorescent ion indicators and metal ions may be introduced between the SES elements of respective clusters of SES elements in FIG. 1A, according to an example of the present disclosure.

In another example, the non-fluorescent ion indicators 502 and the metal ions 504 may be combined into complexes 510 prior to the partial collapse of nano-fingers 104. This example is depicted in FIG. 5C, which shows a simplified side view of a SEFS apparatus 100 in which a solution containing complexes 510 of non-fluorescent ion indicators 502 and metal ions 504 may be introduced between the SES elements 106 of respective clusters 110 of SES elements 106. In this example, following the partial collapse of the nano-fingers 104, for instance, at block 206 in FIG. 2, the complexes 510 may be trapped between the SES elements 106.

Figure 6:
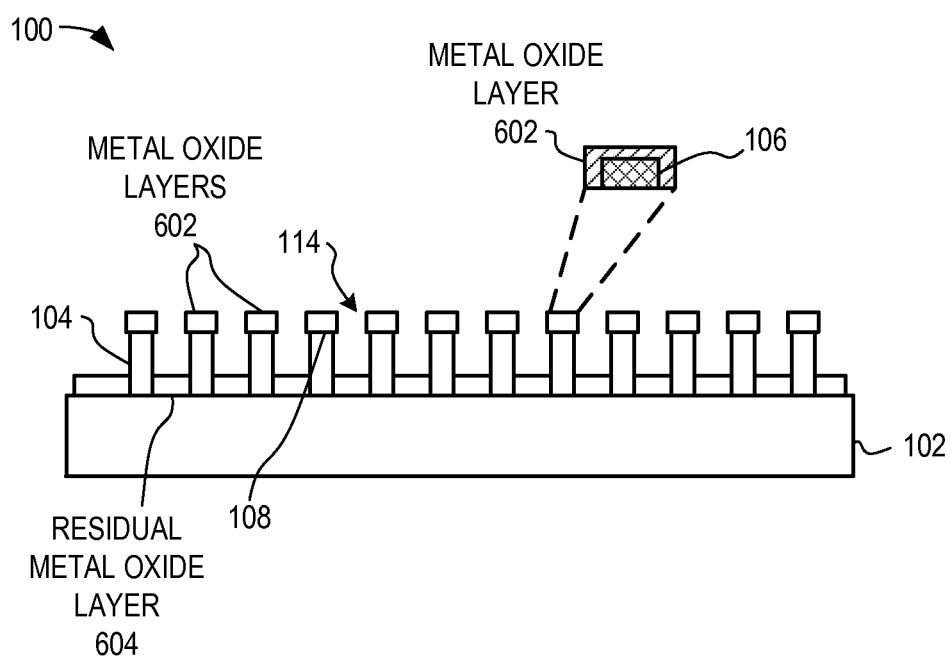
FIG. 6 shows a simplified side view of a SEFS apparatus in which metal oxide layers may respectively be formed on the SES elements prior to introduction of the fluorescence enhancing elements in FIG. 1A, according to an example of the present disclosure.

According to a yet further example, as shown in FIG. 6, metal oxide layers 602 may be respectively formed on the SES elements 106 prior to introduction of the fluorescence enhancing elements 112, for instance at block 204 of FIG. 2. In one regard, the metal oxide layers 602 may be formed on the SES elements 106 to protect the SES elements 106. The metal oxide layers 602 may include, for instance, silicon dioxide ($SiO_2$), titanium oxide ($TiO_2$), zinc oxide (ZnO), aluminum oxide, gallium oxide, indium oxide, zirconium oxide, hafnium oxide, tantalum oxide, and mixtures thereof. The metal oxide layers 602 may be formed through any of a number of metal oxide deposition techniques, such as atomic layer deposition (ALD), E-beam sputtering, etc. In addition, according to an example, the metal oxide layers 602 may be formed to have thicknesses that may vary from about 1 nm to about 200 nm. In another example, the thicknesses of the metal oxide layers may be from about 2 nm to about 50 nm.

Also shown in FIG. 6 is a residual metal oxide layer 604 that may be formed on the substrate 102 between the nano-fingers 104 during the formation of the metal oxide layers 602. An enlarged cross-sectional depiction of one of the SES elements 106 covered by a metal oxide layer 602 is further shown in FIG. 6. As shown in the enlarged cross-sectional depiction, the metal oxide layer 602 may cover the sides and the tops of the SES element 106. In this regard, when the nano-fingers 104 are partially collapsed, for instance, as shown in FIG. 1A, metal oxide layers 602 may be positioned between the SES elements 106 on adjacent ones of the nano-fingers 104. In addition, therefore, instead of contacting the SES elements 106, the fluorescence enhancing elements 112 may contact the metal oxide layers 602 when the fluorescence enhancing elements 112 are trapped in respective clusters 110 of the SES elements 112.

The metal oxide layers 602 may be formed on the SES elements 106 prior to the partial collapse of the nano-fingers 104 to trap any of the fluorescence enhancing elements 112 discussed above. Thus, for instance, the metal oxide layers 602 may be formed on the SES elements 106 prior to introduction of the fluorescence enhancing elements 112, in which the fluorescence enhancing elements 112 are a fluorescent dye.

As another example, the metal oxide layers 602 may be formed on the SES elements 106 prior to introduction of the fluorescence enhancing elements 112, in which the fluorescence enhancing elements 112 are fluorescent probe molecules 402 that are to bind with target molecules 404, for instance, as discussed above with respect to FIG. 4A. As a further example, the metal oxide layers 602 may be formed on the SES elements 106 prior to introduction of the fluorescence enhancing elements 112, in which the fluorescence enhancing elements 112 are complexes 410 of fluorescent probe molecules 402 and target molecules 404, for instance as discussed above with respect to FIG. 4B.

As a yet further example, the metal oxide layers 602 may be formed on the SES elements 106 prior to introduction of the fluorescence enhancing elements 112, in which the fluorescence enhancing elements 112 are non-fluorescent ion indicators 502 that are to bind with predetermined metal ions 504, for instance, as discussed above with respect to FIG. 5B. As a yet further example, the metal oxide layers 602 may be formed on the SES elements 106 prior to introduction of the fluorescence enhancing elements 112, in which the fluorescence enhancing elements 112 are complexes 510 of non-fluorescent ion indicators 502 and metal ions 504, for instance, as discussed above with respect to FIG. 5C.

Although described specifically throughout the entirety of the instant disclosure, representative examples of the present disclosure may have utility over a wide range of applications, and the above discussion is not intended and should not be construed to be limiting, but is offered as an illustrative discussion of aspects of the disclosure.

What has been described and illustrated herein is an example along with some of its variations. The terms, descriptions and figures used herein are set forth by way of illustration only and are not meant as limitations. Many variations are possible within the spirit and scope of the subject matter, which is intended to be defined by the following claims—and their equivalents—in which all terms are meant in their broadest reasonable sense unless otherwise indicated.

What is claimed is:

1. A method for forming a surface-enhanced fluorescence spectroscopy (SEFS) apparatus, said method comprising:
    depositing first, second and third surface-enhanced spectroscopy (SES) elements onto respective tips of first, second and third nano-fingers, wherein the first, second and third nano-fingers are arranged in sufficiently close proximities to each other to enable the tips of the first, second, and third nano-fingers to come into sufficiently close proximities to each other to enable the first, second and third SES elements on the tips to trap a fluorescence enhancing element when the first, second and third nano-fingers are partially collapsed;
    introducing the fluorescence enhancing element between the first, second and third SES elements; and
    causing the first, second and third nano-fingers in the group of adjacent nano-fingers to partially collapse toward each other to cause the first, second and third SES elements on the tips of the first, second, and third nano-fingers in the group to come into sufficiently close proximities to each other to trap a fluorescence enhancing element between and in mutual concurrent contact with each of the first, second and third SES elements.

2. The method according to claim 1, wherein the fluorescence enhancing element comprises a fluorescent dye.

3. The method according to claim 1, wherein the fluorescence enhancing element is a fluorescent probe molecule that binds with target molecules, said method further comprising:
    introducing a solution containing the target molecules onto the fluorescence enhancing element and the first, second, and third, wherein the target molecules bind with the fluorescent probe molecule.

4. The method according to claim 1, wherein the fluorescence enhancing element is a fluorescent probe molecule that binds with target molecules, said method further comprising:
    combining the fluorescent probe molecule and the target molecules in a solution, wherein the fluorescent probe molecule binds with the target molecules in the solution; and
    wherein introducing the fluorescence enhancing element onto the first, second, and third further comprises introducing the combined fluorescent probe molecule and the target molecules onto the first, second, and third.

5. The method according to claim 1, wherein the fluorescence enhancing element comprises a complex formed of non-fluorescent ion indicators that are selectively bound to predetermined metal ions, said method further comprising:
    combining the non-fluorescent ion indicators and the predetermined metal ions; and
    wherein introducing the fluorescence enhancing element onto the first, second, and third further comprises introducing the non-fluorescent ion indicators or the combination of the non-fluorescent ion indicators and the predetermined metal ions onto the first, second, and third.

6. The method according to claim 1, further comprising:
    forming respective layers of metal oxide onto the first, second, and third prior to introducing the fluorescence enhancing element; and
    wherein introducing the fluorescence enhancing element further comprises introducing the fluorescence enhancing element onto the metal oxide layers on the first, second, and third.

7. The method according to claim 6, wherein the fluorescence enhancing element comprises a fluorescent dye.

8. The method according to claim 6, wherein the fluorescence enhancing element is a fluorescent probe molecule that binds with target molecules, said method further comprising:
    introducing a solution containing the target molecules onto the fluorescence enhancing elements and the metal oxide layers, wherein the target molecules bind with the fluorescent probe.

9. The method according to claim 6, wherein the fluorescence enhancing element is a fluorescent probe molecule that binds with target molecules, said method further comprising:
   combining the fluorescent probe molecule and the target molecules in a solution, wherein the fluorescent probe molecules are to bind with the target molecules in the solution; and
   wherein introducing the fluorescence enhancing element onto the metal oxide layers further comprises introducing the combined fluorescent probe molecule and the target molecules onto the metal oxide layers.

10. The method according to claim 6, wherein the fluorescence enhancing element comprises a complex formed of non-fluorescent ion indicators that are selectively bound to predetermined metal ions, said method further comprising:
   combining the non-fluorescent ion indicators and the predetermined metal ions; and
   wherein introducing the fluorescence enhancing element onto the metal oxide layers further comprises introducing the non-fluorescent ion indicators or the combination of the non-fluorescent ion indicators and the predetermined metal ions onto the metal oxide layers.

11. A surface-enhanced fluorescence spectroscopy (SEFS) apparatus comprising:
   a substrate having first, second and third nano-fingers;
   first, second and third surface-enhanced spectroscopy (SES) elements supported on first, second and third tips of the first, second and third nano fingers, respectively, wherein the first, second and third nano fingers are partially collapsed onto each other to position the first, second and third SES elements in at least one of contact with and close proximity to each other;
   a metal oxide layer formed on each of the first, second and third SES elements; and
   a fluorescence enhancing element trapped between and in mutual concurrent contact with each of the first, second and third SES elements as a result of the partial collapse of the first, second and third nano fingers.

12. The SEFS apparatus according to claim 11, wherein the fluorescence enhancing element comprises a fluorescent dye.

13. The SEFS apparatus according to claim 11, wherein the fluorescence enhancing element is a fluorescent probe molecule bound to with target molecules.

14. The SEFS apparatus according to claim 11, wherein the fluorescence enhancing element comprises a complex formed of non-fluorescent ion indicators that are selectively bound to predetermined metal ions.

* * * * *

UNITED STATES PATENT AND TRADEMARK OFFICE
CERTIFICATE OF CORRECTION

PATENT NO. : 9,702,821 B2
APPLICATION NO. : 14/762415
DATED : July 11, 2017
INVENTOR(S) : Zhang-Lin Zhou et al.

Page 1 of 1

It is certified that error appears in the above-identified patent and that said Letters Patent is hereby corrected as shown below:

Column 12, Line 12, Claim 1, delete "a" and insert -- the --, therefor.

Column 12, Line 67, Claim 8, delete "probe." and insert -- probe molecules. --, therefor.

Signed and Sealed this
Twenty-seventh Day of February, 2018

Andrei Iancu
*Director of the United States Patent and Trademark Office*